United States Patent [19]

Mack

[11] 4,172,207

[45] Oct. 23, 1979

[54] PROCESS FOR MERCAPTOALKANEDICARBOXYLIC ACID ESTERS

[76] Inventor: Gerry P. Mack, 34-28 86th St., Jackson Heights, N.Y. 11372

[21] Appl. No.: 770,823

[22] Filed: Feb. 22, 1977

[51] Int. Cl.$^2$ .................. C07C 148/00; C07C 149/20
[52] U.S. Cl. ................................ 560/147; 260/326.44; 260/326.5 S; 260/346.74; 260/455 R; 562/594
[58] Field of Search .................. 260/346.8 R, 326.5 S, 260/326.44, 537 S, 455 R, 346.74; 560/147; 562/594

[56] References Cited

FOREIGN PATENT DOCUMENTS 542641  1/1942  United Kingdom ................ 260/481 R Primary Examiner—Vivian Garner
Attorney, Agent, or Firm—Otto S. Kauder

[57] ABSTRACT

A process is provided for the preparation of mercaptoalkane 1,2-dicarboxylic acid esters from readily available starting materials such as hydrogen sulfide and unsaturated alkene 1,2-dicarboxylic acid compounds. Isolation of the intermediate mercaptoalkanedicarboxylic acid can be avoided when a mercaptoalkanedicarboxylic acid ester is the desired product.

12 Claims, No Drawings

PROCESS FOR MERCAPTOALKANEDICARBOXYLIC ACID ESTERS

BACKGROUND OF THE INVENTION

This invention pertains to a practical and economical process for the production of mercaptoalkanedicarboxylic acids and esters of the same. In a particular aspect this invention concerns the production of thiomalic acid and its esters.

Conventionally, mercaptoalkanedicarboxylic acid esters have been prepared by esterification of the corresponding acid, and hence their availability and manufacture have depended on the availability and manufacture of the mercaptoalkanedicarboxylic acid. While mercaptoalkanedicarboxylic acids have been known for many years, they have never reached large volume industrial production and have remained high cost products.

The simplest mercaptoalkanedicarboxylic acid, thiomalic acid or 2-mercaptobutanedioic acid, is a polyfunctional compound which undergoes the typical reactions of mercaptans and dicarboxylic acids. It is used in the pharmaceutical field, particularly with heavy metals where the sodium salt is less toxic than 2,3-dimercaptopropanol and more effective against poisoning by bismuth, mercury, or arsenic. Thiomalic acid has been reported to reduce the color of crepe rubber and to tackify butadiene type synthetic rubber as disclosed by W. Sharkey in U.S. Pat. No. 2,449,418 of Sept. 14, 1948. Esters of thiomalic acid have been disclosed as air hardening coating compounds by B. Pratt in U.S. Pat. No. 2,456,314 of Dec. 14, 1948 and as ingredients and reactants for the preparation of organotin mercaptocarboxylic acid ester stabilizer compositions for polyvinyl chloride by E. Weinberg in U.S. Pat. Nos. 2,648,650 of Aug. 11, 1953 and 2,832,752 of Apr. 29, 1958; by G. P. Mack in U.S. Pat. No. 2,914,506 of Nov. 24, 1959 and by L. R. Brecker in U.S. Pat. Nos. 3,642,848 of Feb. 15, 1972 and 3,674,737 of July 4, 1972.

Methods heretofore proposed for the production of thiomalic acid are not generally suited for commercial scale operations, primarily because of the poor yields they afford and the length of the reaction period required. Furthermore, yields in actual practice have been found to vary substantially even though the process conditions are most carefully controlled, and this is due to the fact that the thiomalic acid is highly soluble in water and partition coefficients against extracting solvents are unfavorable. With several extractions needed during its recovery, much thiomalic acid can therefore be oxidized to undesirable by-products.

Thiomalic acid may be prepared from maleic acid and hydrogen sulfide in a variety of ways. In British Pat. No. 670,702 the method is described using maleic acid and sodium hydrosulfide in the presence of sodium hydroxide. The sodium hydrosulfide should be prepared by using hydrogen sulfide and an excess of sodium hydroxide as is well known in the literature.

According to EXAMPLE 1 in the above British Patent, the preparation of thiomalic acid, it takes a considerable amount of time, 19½ hours, and the resulting acidification of the reaction mixture to give crude thiomalic acid gives only about 35% yield of the crude acid based on the maleic acid charged. Concentration of the mother liquors is necessary to give an additional 38% of product. It is then necessary to recrystallize from water and then from ethyl acetate to purify the thiomalic acid. No finished yield is given in this example although it was shown that a 87% yield of mercaptan had been formed in the solution by titration. It has been found in practice that the actual yield of thiomalic acid after going through the concentration of mother liquors, recrystallization etc., is of a lower order, approximately 25-30%. The large loss in yield is due to the similar solubilities of thiomalic acid and by product sodium chloride both in water and in ethyl acetate. It is also necessary to recrystallize the product due to the impurities formed such as the disulfides and other compounds such as the thioether thiodisuccinic acid, and inorganic salts.

The reaction of hydrogen sulfide with esters of maleic acid and with maleic anhydride are also known, but these reactions take a completely different course. As disclosed by L. Newton in U.S. Pat. No. 2,603,616 of July 15, 1952, hydrogen sulfide and an alkene 1,2-dicarboxylic ester such as dibutyl maleate react smoothly in the presence of a tertiary amine catalyst to give tetrabutyl 2,2'-thiodisuccinate, a thioether ester rather than a mercaptan derivative. Newton indicates that at best a small quantity of mercaptoalkanedicarboxylic acid ester might have been obtainable by this reaction since the reaction of mercaptoalkanedicarboxylic ester with alkenedicarboxylic acid ester is more rapid than the reaction of the latter with hydrogen sulfide. F. Zienty in Journal of Organic Chemistry, Vol. 27 (1962) page 3144 stated that "Maleic anhydride does not react with hydrogen sulfide in benzene solution in the absence of a basic catalyst; the solution remains colorless and the maleic anhydride is recovered unchanged. With base present in catalytic amounts, reaction with maleic anhydride occurs as rapidly as hydrogen sulfide is introduced to the reaction mixture. Under a variety of conditions and ratios of reactants the product obtained is in every case the adduct of two moles of maleic anhydride and one of hydrogen sulfide. There is no evidence that the reaction can be interrupted at the 1:1 addition stage".

Another synthesis for forming thiomalic acid is by the reaction of thioacetic acid and maleic acid as cited in Flett and Garner's, "Maleic Anhydride Derivatives", (J. Wiley, New York 1952) page 225. The example given here uses thioacetic acid plus maleic acid to give mercaptosuccinic acid acetate having the formula

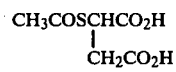

and the yield is 83% of that required by theory for the latter but no yield is given for the subsequent alkaline hydrolysis of this acetate to disodium thiomalate and sodium acetate and the eventual acidification to give thiomalic acid. This procedure is impractical in that the thioacetic acid preparation is expensive and is not commercially available on a large scale at an economical price, and thus is a drawback to this process. Moreover, once thiomalic acid is obtained by alkaline hydrolysis of the acetate and acidification, it must still be isolated from the water solution containing inorganic salts, just as in the sulfide process of the British patent already discussed.

As discussed above the sulfide procedure is uneconomical because of low yield and the necessity to remove by-products by recrystallization in solvents, which are expensive and cause hazards. At least some of these difficulties apply equally to the thioacetic acid procedure.

At present time there is a need for a commercial process that is economical for preparing thiomalic acid and its esters so that many valuable industrial products can be made.

My process overcomes the numerous disadvantages among which is the fact that the processes are inconvenient or dependent on expensive intermediates to prepare thiomalic acid or esters.

SUMMARY OF THE INVENTION

According to my invention, a process for producing a mercaptoalkane 1,2-dicarboxylic acid alkyl ester having 2 to 3 carbon atoms in the alkane group and 1 to about 24 carbon atoms in the alkyl ester group comprises the steps of forming a reaction mixture comprising hydrogen sulfide, acetic anhydride, and an alkene-1,2-dicarboxylic acid compound selected from the group consisting of alkenedicarboxylic acids, alkenedicarboxylic anhydrides, alkenedicarboxylic esters, alkenedicarboxylic amides, and alkenedicarboxylic imides; heating the reaction mixture at 30° to 230° C. to form an S-acetylthioalkane-1,2-dicarboxylic acid compound in the reaction mixture; heating the mixture comprising S-acetylthioalkanedicarboxylic acid compound with a selective deacetylating agent to form a mercaptoalkane-1,2-dicarboxylic acid compound in the mixture; adding as needed alcohol having 1 to about 24 carbon atoms to the reaction mixture and heating to convert to mercaptoalkane-1,2-dicarboxylic acid alkyl esters mercaptoalkane-1,2-dicarboxylic acid compounds that are not already mercaptoalkane-1,2-dicarboxylic acid alkyl esters; and recovering mercaptoalkane-1,2-dicarboxylic acid alkyl ester from the reaction mixture. The process can be operated in the absence of catalysts or solvents and at atmospheric, subatmospheric or superatmospheric pressures as desired. The selective deacetylating agent accomplishes the conversion of the S-acetylthioalkane-1,2-dicarboxylic acid compound to a mercaptoalkane-1,2-dicarboxylic acid compound that is a mercaptoalkane-1,2-dicarboxylic acid or is a mercaptoalkane-1,2-dicarboxylic acid alkyl ester or can be readily converted to such ester without requiring the isolation of mercaptoalkane-1,2-dicarboxylic acid from a solution containing such acid along with large quantities of inorganic salt. If desired, the the ester can be converted to the acid and the acid recovered.

DESCRIPTION OF THE PREFERRED EMBODIMENTS

The mercaptoalkane-1,2-dicarboxylic acid alkyl esters prepared according to this invention are esters of mercaptoethane-1,2-dicarboxylic acid (also known as thiomalic acid), made from ethene-1,2-dicarboxylic acid (whose isomers are commonly known as maleic and fumaric acids) or an ester, amide, imide, or anhydride thereof; 1-mercaptopropane-1,2-dicarboxylic acid esters from cis- and trans-1-propene-1,2-dicarboxylic acid (i.e. citraconic or mesaconic acid) or ester, amide, imide, or anhydride; and 3-mercaptopropane-1,2-dicarboxylic acid esters from 2-propene-1,2-dicarboxylic acid (i.e. itaconic acid) or ester, amide, imide, or anhydride. The chemical reactions that take place in the preparation of mercaptoalkane-1,2-dicarboxylic acid alkyl esters according to this invention are illustrated in Scheme 1 below for the case where the alkene-1,2-dicarboxylic acid compound starting material is maleic acid and the esterifying alcohol is n-butanol.

SCHEME 1

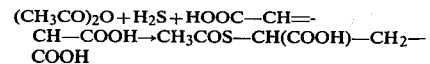

In this first step, the addition of acetic anhydride and hydrogen sulfide to maleic acid produces 2-S-acetylthiosuccinic acid.

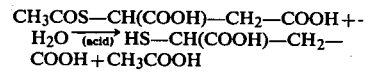

In this second step, selective deacetylation takes place to give thiomalic acid in solution. If desired this thiomalic acid can be isolated.

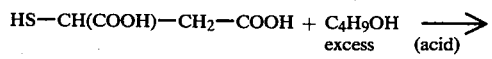

In this third step, thiomalic acid and acetic acid are esterified with butanol. The two esters are easily separated by distillation.

When the alkene-1,2-dicarboxylic acid compound starting material is an ester, such as diethyl fumarate, the addition of acetic anhydride and hydrogen sulfide proceeds to give the diethyl ester of S-acetylthiosuccinic acid, which on selective deacetylation, suitably by means of aqueous alcoholic ammonia, gives diethyl thiomalate according to this invention, as illustrated in SCHEME 2 below.

SCHEME 2

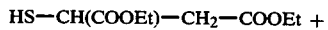

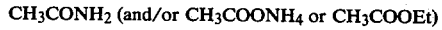

When the alkene-1,2-dicarboxylic acid compound starting material is an amide or imide, the addition of acetic anhydride and hydrogen sulfide gives the amide or imide of S-acetylthiosuccinic acid. Selective deacetylation of this amide or imide can be accomplished with aqueous alcoholic ammonia to give the amide or imide of a mercaptoalkane-1,2-dicarboxylic acid. The latter can be converted to an alkyl ester of mercaptoalkane-1,2-dicarboxylic acid according to this invention suitably by acid-catalyzed alcoholysis in the presence of sufficient acid to neutralize the side product ammonia or amine resulting from the conversion of amide or imide groups to ester. In SCHEME 3 below, these reactions are illustrated for the case of the conversion of N-ethylmaleimide to di-2-ethylhexyl thiomalate by the process of this invention:

SCHEME 3

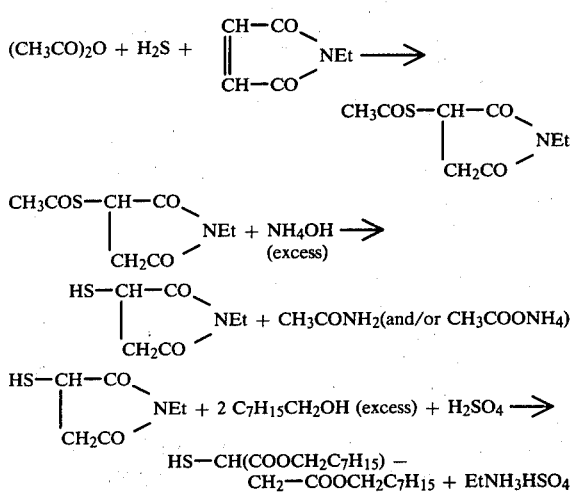

Esterifying alkyl groups in the alkyl esters prepared according to this invention and in alkyl ester starting materials or in alcohols used to prepare the alkyl esters have 1 to about 24 carbon atoms, and are preferably primary or secondary alkyl groups. Suitable alkyl groups include methyl, ethyl, n-propyl, isopropyl, n-butyl, sec-butyl, isobutyl, isoamyl, methylisobutylcarbinyl, 2-ethylbutyl, n-hexyl, n-heptyl, n-octyl, isooctyl, 2-ethylhexyl, isononyl, 3,3,5-trimethylhexyl, n-decyl, isodecyl from the OXO process, n-dodecyl, tridecyl from the OXO process, and tetradecyl as well as mixtures resulting from the use of commercially available alcohol mixtures such as mixed 20 to 24 carbon atom alcohols from the alkylaluminum process or mixed 7 to 11 carbon atoms and 12 to 14 carbon atom alcohols from the OXO process applied to linear olefins.

Alkene-1,2-dicarboxylic acid amide or imide starting materials can be unsubstituted or substituted on the nitrogen of amide or imide groups. Substituents when present can be phenyl, alkyl of 1 to about 4 carbon atoms, and hydroxyalkyl of 2 to 3 carbon atoms.

As shown in Schemes 1, 2, and 3 above, my process requires the use of one mole of acetic anhydride and one mole of hydrogen sulfide per mole of alkene-1,2-dicarboxylic acid compound converted. In practice, an excess of acetic anhydride is helpful in achieving as nearly complete conversion as possible of the alkene-1,2-dicarboxylic acid compound in a reasonable reaction time. A suitable excess ranges from 0.1 to about 2 moles acetic anhydride in addition to each mole required according to the reaction equation. Larger excesses can also be used but are subject to diminishing economic returns. The proportion of hydrogen sulfide in the reaction is largely self-regulated as the solubility of hydrogen sulfide in the reaction system at any time is approximately the amount that can react, and to the extent the reaction takes place additional quantities dissolve as long as the supply of hydrogen sulfide to the reaction system continues.

The selective deacetylating agent used according to the process of this invention accomplishes the deacetylation of the S-acetylthioalkane-1,2-dicarboxylic acid compound to a mercaptoalkane-1,2-dicarboxylic acid compound without at the same time generating a water soluble salt form of the mercaptoalkane-1,2-dicarboxylic acid compound. Useful selective deacetylating agents include water, organic sulfonic acids, alcohols, having 1 to about 24 carbon atoms, ammonia, non-aromatic tertiary amines having 3 to about 12 carbon atoms, and catalytic quantities, i.e. less than 0.1 mole per mole of S-acetylthioalkane-1,2-dicarboxylic acid compound of fixed bases and basic salts such as sodium bicarbonate, potassium hydroxide, sodium methylate, potassium t-butoxide, barium oxide, potassium cyanide, sodium sulfide, and sodium sulfite. Combinations of these agents are frequently very useful, depending in part on the particular S-acetylthioalkane-1,2-dicarboxylic acid compound to be selectively deacetylated. Particularly useful combinations include water and hydrochloric acid; aqueous ammonia and a water miscible alcohol especially isopropyl alcohol; sulfuric acid and a water-immiscible alcohol; isobutyl alcohol with a catalytic quantity of methanesulfonic acid; and methanol with a catalytic quantity of potassium carbonate. When an alcohol is used as a selective deacetylating agent, it is conveniently the same alcohol whose mercaptoalkane-1,2-dicarboxylic acid ester is being prepared. Alternatively, isopropyl alcohol can be used as a selective deacetylating agent with relatively little tendency to esterify the carboxylic acid groups.

The process of this invention can be operated over a range of conditions. Temperatures during the addition of acetic anhydride and hydrogen sulfide to the alkene-1,2-dicarboxylic acid compound can be in the range of 30° to 230° C., preferably 50°-100° C.; during the selective deacetylation and conversion to mercaptoalkane-1,2-dicarboxylic acid ester any temperature not exceeding 160° C., preferably about 50° to 140° C., can be used. The pressure can be atmospheric, superatmospheric from 1 up to about 20 kg per square centimeter, or subatmospheric from 760 mm down to about 20 mm of mercury as desired. Special solvents are not usually required; those of the reactants that are liquid at the reaction temperature can serve as solvents for the remaining reactants. Polar solvents that can be advantageous to use include esters such as ethyl acetate and butyl acetate, ethers and ether alcohols such as tetrahydrofuran, diglyme, and 2-methoxyethanol, sulfur compounds such as tetramethylene sulfone and 2-ethanesulfonylethanol, and amides such as formamide, dimethylformamide, and tetramethylurea.

Catalysts are not essential for the operation of the process according to the invention but can be used if desired to increase the rate of reaction or lower the reaction temperature. Acidic or basic catalysts can be used. Acidic catalysts include organic sulfonic acids such as methanesulfonic acid, benzenesulfonic acid and polystyrenesulfonic acid; inorganic acids such as phosphorous acid, phosphoric acid, hydrobromic acid, hydrochloric acid, sulfamic acid, and sulfuric acid. Basic catalysts include the fixed bases and basic salts already mentioned and organic tertiary amines such as pyridine, picoline, collidine, lutidine trimethylamine, triethylamine, benzyldimethylamine, triethylenediamine, and dimethylaminoethanol.

At least one mole of the selective deacetylating agent is used per mole of S-acetylthioalkane-1,2-dicarboxylic acid compound. The agent is usually used in excess over that theoretically required, and the excess of such agent can be recovered if necessary since little or none of it is consumed in unwanted side reactions. When the selective deacetylating agent is an alcohol also serving to esterify the dicarboxylic acid compound and form the desired mercaptoalkane-1,2-dicarboxylic acid ester, the required amount is three moles per mole of S-acetylthioalkane-1,2-dicarboxylic acid compound, and the use of an excess over this amount is helpful.

The isolation and recovery of the desired mercaptoalkane-1,2-dicarboxylic acid ester can be accomplished by conventional techniques such as liquid-liquid extraction, distillation, and sometimes crystallization.

My process is unique in the preparation of the esters of thiomalic acid or thiomalic acid itself by forming S-acetylthiosuccinic ester from a maleic acid ester through the process consisting of reacting hydrogen sulfide and the ester of maleic acid in the presence of suitable amounts of acetic anhydride at elevated temperatures or at lower temperatures with a catalyst, then hydrolyzing the resulting S-acetylthiosuccinic ester with aqueous ammonium hydroxide to give a desired thiomalic acid ester which then can be removed from the reaction mixture by distillation. Through this unique process nearly quantitative yields of the desired thiomalic acid or ester can be obtained. This process can be extended for reactions with other maleic acid derivatives such as the amides, imides, and also to other double bond containing compounds as for instance vinyl esters, acrylates, and vinylethers.

In the case of the thiomalic acid itself it can be readily obtained in practically quantitative yields by starting with dimethyl maleate and converting it to dimethyl thiomalate by my process and then hydrolyzing this under acidic or mild alkaline catalyzed conditions using less than stoichiometric quantities of alkali to give thiomalic acid directly.

My process is also very economical in preparing organotin compounds of thiomalic derivatives as outlined in my copending application Ser. No. 646,310, now U.S. Pat. No. 4,058,543, where in this procedure there is no need to separate out or distil the thiomalic esters but can convert them directly to an organotin stabilizer as shown later.

The thiomalic acid can be prepared directly in my process as mentioned by preparing the acetylated product of dimethylmaleate and then hydrolyzing this directly with mild alkali and recovering the methyl alcohol. Of course the alcohol can be recovered and used for the preparation of thiomalic methyl esters; this cyclic process has significant economic advantages. The process also avoids the formation of disulfides while permitting the preparation in high yield of thiomalic acid.

The following examples are offered by way of illustration but not by way of limitation.

EXAMPLE 1

Preparation of Dibutyl Thiomalate

In a suitable 3 neck reaction flask set up with heating mantle, stirrer, thermometer, and sparging tubes are placed 342.4 grams (1½ moles) dibutylmaleate; 2.0 grams potassium hydroxide powdered, 209 grams acetic anhydride. Heating is started at 50°–60° C.; via a sparging tube $H_2S$ is slowly added while agitating the reaction mixture. After 3 hours 55–57 grams weight increase is obtained and the $H_2S$ addition is discontinued.

The temperature is now raised to 90°–100° C. and held for 4 hours. The reaction mass is then washed two times with approximately 300 cc of hot water and then with 300 cc of 10% $NH_4OH$.

The reaction mixture is filtered through Supercel or similar material and a yield of approximately 95% of S-acetyldibutylthiomalate is obtained.

The reaction flask is set up for reflux with a thermometer and agitator. There is added approximately 800 grams of the above S-acetyldibutylthiomalate, 500 cc water, 225 cc of isopropanol and the agitation is started, the mixture is brought up to 60°–70° C. At this point 350 cc of 29% ammonia solution is added and after 2 hours of refluxing additional 450 cc of ammonia solution is added. The mixture is cooled to 10°–15° C. and neutralized while stirring with 17–25 cc of 10% HCl over a period of 6 to 8 hours.

The product is washed with 2–300 cc of warm water and a final wash of 500 cc of warm water. The product is decanted and then dried and a dibutylthiomalate yield of approximately 88% is obtained.

The product dibutylthiomalate is analyzed and found to have a mercapto sulfur content of 12.15% and a total sulfur of 12.30%. The latter was done by the oxygen flask combustion method of determining sulfur. (Theory requires 12.21% sulfur).

This example shows that the preparation of dibutylthiomalate according to this invention gives a better overall yield and is much simpler in operation than known processes for this preparation.

EXAMPLE 2

Dimethylthiomalate

Example 1 was repeated but in place of the dibutylmaleate, dimethylmaleate 1½ moles was used and the same procedure was followed and dimethylthiomalate obtained in 90% yield. Analysis for mercapto and total sulfur were 17.4% mercapto sulfur, 17.1% Total sulfur. (Theory requires 17.97% sulfur).

EXAMPLE 3

Dibutylthiomalate

The above procedure was repeated with dibutylmaleate and pyridine 1.5 grams was used as a catalyst.

The rest of the procedure is identical as EXAMPLE 1 and a 92% yield of dibutylthiomalate was obtained having the same analysis as in EXAMPLE 1.

EXAMPLE 4

Di-n-octylthiomalate

The above was repeated except for using dioctylmaleate and similar results were obtained. A yield of 90% was obtained and the product was analyzed and had 8.4% mercapto sulfur and 8.62% total sulfur. (Theoretical sulfur content is 8.82%).

EXAMPLE 5

Dilaurylthiomalate

The above was repeated using dilauryl maleate and after the same exact conditions were used the final product was dilaurylthiomalate in approximately 89% yield and analysis indicated that it had 5.62% by weight of mercaptosulfur and 5.95% total sulfur. For most applications the above can be used as such but where a high pure product is desired then the thiomalic esters can be distilled under vacuum.

EXAMPLE 6

Thiomalic acid

To form thiomalic acid, the procedure of EXAMPLE 2 was repeated with dimethylmaleate and 178 g of the finished dimethylthiomalate was then placed in a reaction flask with approximately 400 cc of water, in which 15 g of 35% concentrated HCl was dissolved and while sitrring rapidly the mixture was refluxed for 8 hours.

The reaction mixture was distilled under 10 mm vacuum to remove the methanol and HCl. The mixture was then placed in a vacuum oven to remove the water to give thiomalic acid in approximately 88% yield which had a melting point of 152°–156° C. By titrating with standard alkali equivalent weight of 76 was obtained whereas the theoretical equivalent weight of thiomalic acid is 75.5.

My process is highly efficient and low cost for preparing intermediates such as the ethylene glycol bis alkylthiomalate that is used in producing the organotin stabilizers as set forth in my copending application Ser. No. 646,310 now U.S. Pat. No. 4,058,543.

EXAMPLE 7

Ethylenebis(butylthiomalate) from dibutylmaleate

EXAMPLE 1 is repeated and after the product is dried it is directly reacted with ethylene glycol to give the ester ethyleneglycol bis(butylthiomalate).

The simple procedure would be to charge 524 grams or 2 moles of dibutylthiomalate, 62 grams or 1 mole of ethyleneglycol, 100 grams of benzene, and 2 grams of p-TSA catalyst. This is refluxed for 4 hours and then set up for distillation under vacuum and 150 grams of butanol are stripped off to give the product having the structure

This is ethyleneglycol bis(butylthiomalate) and an assay of mercapto sulfur gives 14.5%. Theoretical sulfur equals 15.13%. This product is suitable for the preparation of the organotin stabilizers as outlined in my pending application Ser. No. 646,310 now U.S. Pat. No. 4,058,543.

Another very economical procedure for making the intermediate suitable for preparing organotin stabilizers as for my copending application Ser. No. 646,310 now U.S. Pat. No. 4,058,543.

EXAMPLE 8

Ethylene bis(butylthiomalate) from maleic anhydride

In a reaction flask set up as in EXAMPLE 1 was charged 320 grams of ethylacetate with 174 grams maleic anhydride (1.75 moles) and 32 grams of water. The temperature was slowly raised to 80° C. and then acetic anhydride 360 g (3.5 moles) and pyridine 15 g were added. The temperature stabilized at 45° C. and hydrogen sulfide from a cylinder was passed in for 4 hours. Weight gain of the reaction mixture was 59 g.

The above mixture was then heated to reflux and after about 4 hours there was no H₂S odor and zero titration with iodine-potassium iodine solution, indicating there was formed S-acetyldibutylthiomalic acid.

While refluxing the above, a solution containing 10 cc of concentrated HCl and 100 cc of water was slowly added and refluxing was continued for 2 to 2½ hours to complete reaction, as shown by the titration with iodine-potassium iodide solution increasing to a constant value, representing the formation of thiomalic acid in solution.

To this was then added 675 grams of n-butanol, 20 cc of benzene and 3.5 grams of para-toluenesulfonic acid. This mixture was then azeotroped until no more water came over and then 165 grams of ethyleneglycol was added and a distillation set-up was set up. Distillation under vacuum was used to strip or remove the ethyl acetate, excess butanol, and sufficient butanol resulting from transesterification to give a product having approximately the following structure:

The product was assayed for mercapto sulfur which was 14.1%.

436 (about 1 mole) of this product was then treated with 90 g monobutyltin oxide and 60 g dibutyltin oxide to prepare a mixed mono/di butyltin compound. When this was used as a stabilizer for PVC excellent results were obtained and comparable to a stabilizer obtained under the same conditions except that the dibutylthiomalate used in preparing the bis(ethyleneglycol) dibutylmalate was highly purified having a 14.6% mercaptan sulfur content (the theoretical mercaptan sulfur content is 15.13%).

I claim:

1. A process for producing a mercaptoalkane-1,2-dicarboxylic acid alkyl ester having 2 to 3 carbon atoms in the alkane group and 1 to about 24 carbon atoms in the alkyl group comprising the steps of first, forming a reaction mixture comprising hydrogen sulfide, acetic anhydride, and an alkene 1,2-dicarboxylic acid compound selected from the group consisting of alkene 1,2-dicarboxylic acids, alkene-1,2-dicarboxylic anhydrides, alkene-1,2-dicarboxylic esters, alkene-1,2-dicarboxylic amides, and alkene-1,2-dicarboxylic imides; second, heating the reaction mixture at 30° to 230° C. to form an S-acetylthio-1,2-alkanedicarboxylic acid compound in the reaction mixture; third, heating the reaction mixture comprising S-acetylthioalkane-1,2-dicarboxylic acid compound with a selective deacetylating agent to form a mercaptoalkane-1,2-dicarboxylic acid compound in the mixture; fourth, adding as needed alcohol having 1 to about 24 carbon atoms to the reaction mixture and heating to convert to mercaptoalkane-1,2-dicarboxylic acid esters mercaptodicarboxylic acid compounds in the mixture that are not mercaptodicarboxylic esters, and fifth, recovering mercaptoalkane-1,2-dicarboxylic acid ester from the reaction mixture.

2. A process according to claim 1 in which the alkene-1,2-dicarboxylic acid compound is an alkene-1,2-dicarboxylic acid alkyl ester having 1 to 24 carbon atoms in each alkyl group.

3. A process according to claim 1 in which the alkene-1,2-dicarboxylic acid compound is selected from the group consisting of maleic acid, maleic anhydride, itaconic acid, and itaconic anhydride.

4. A process according to claim 1 in which the selective deacetylating agent is ammonia.

5. A process according to claim 1 in which the selective deacetylating agent is water.

6. A process according to claim 1 in which the selective deacetylating agent is an alcohol having 1 to 24 carbon atoms.

7. A process according to claim 1 in which an acidic catalyst is used in at least one of the second, third, and fourth steps.

8. A process according to claim 1 in which an alkaline catalyst is used in at least one of the second, third, and fourth steps.

9. A process according to claim 1 in which the selective deacetylating agent is a solution of ammonia in isopropyl alcohol and water.

10. A process for producing a mercaptoalkane-1,2-dicarboxylic acid having 2 to 3 carbon atoms in the alkane group comprising the steps of forming a reaction mixture comprising hydrogen sulfide, acetic anhydride, and an alkene-1,2-dicarboxylic acid compound selected from the group consisting of alkene-1,2-dicarboxylic acids, alkene-1,2-dicarboxylic anhydrides, and alkene-1,2-dicarboxylic esters; heating the reaction mixture at 30° to 230° C. to form an S-acetylthio-1,2-alkanedicarboxylic acid compound in the reaction mixture; heating the reaction mixture comprising S-acetylthioalkane-1,2-dicarboxylic acid compound with a selective deacetylating agent to form a mercaptoalkane-1,2-dicarboxylic acid in the mixture; and recovering mercapto-1,2-alkanedicarboxylic acid from the reaction mixture.

11. A process according to claim 10 in which the mercaptoalkane-1,2-dicarboxylic acid is thiomalic acid.

12. A process according to claim 10 in which the selective deacetylating agent comprises water and an acidic catalyst.

* * * * *